United States Patent [19]

Flynn

[11] Patent Number: 5,735,265
[45] Date of Patent: Apr. 7, 1998

[54] CPR FACE MASK WITH FILTER PROTECTED FROM PATIENT-EXPIRED CONDENSATE

[76] Inventor: Stephen Flynn, 255 Chartwell Road, Oakville, Ontario, Canada, L6J 3Z7

[21] Appl. No.: 755,761

[22] Filed: Nov. 21, 1996

[51] Int. Cl.[6] .................. A61M 16/00; A62B 18/08; A62B 18/10
[52] U.S. Cl. .................. 128/203.11; 128/202.28; 128/206.15; 128/206.29; 128/207.12
[58] Field of Search .................. 128/202.28, 202.29, 128/203.11, 206.15, 206.29, 207.12, 206.21

[56] References Cited

U.S. PATENT DOCUMENTS

| | | | |
|---|---|---|---|
| 4,811,730 | 3/1989 | Milano | 128/202.29 |
| 4,886,057 | 12/1989 | Nave | 128/202.28 |
| 5,005,568 | 4/1991 | Loescher et al. | 128/203.11 |
| 5,121,745 | 6/1992 | Israel | 128/202.28 |
| 5,469,842 | 11/1995 | Flynn | 128/202.28 |
| 5,511,543 | 4/1996 | Shirley | 128/202.28 |

*Primary Examiner*—Kimberly L. Asher
*Attorney, Agent, or Firm*—Rogers & Scott

[57] ABSTRACT

A CPR face mask has a face engaging part positionable on the face of a patient to surround at least the mouth of the patient. An air flow control valve is carried by the face engaging part and has an upper inlet into which air can be blown by a CPR giving person and which passes downwardly through a first outlet into a patient's mouth. The flow control valve causes air passing upwardly from the patient's mouth into the first outlet to be released to the external atmosphere through a second outlet without passing to the inlet. The flow control valve has a flexible diaphragm operable to prevent air flow from the inlet to the second outlet when the CPR giving person is blowing into the inlet and to prevent air flow from the first outlet to the inlet when air passes upwardly from the patient's mouth into the first outlet. A filter is located immediately upstream of the diaphragm with respect to air flow blown into the first inlet by the CPR giving person. The diaphragm having a filter-blocking position assumed during patient exhalation to protect the filter from patient-expired condensate.

4 Claims, 2 Drawing Sheets

CPR FACE MASK WITH FILTER PROTECTED FROM PATIENT-EXPIRED CONDENSATE

FIELD OF INVENTION

This invention relates to CPR face masks, namely face masks which are placed over the mouth of a patient requiring cardiopulmonary resuscitation and through which air can be blown into the patient's mouth by a person giving the CPR.

Such face masks are becoming more widely used to avoid the CPR giving person having to be in direct mouth to mouth contact with the patient and hence minimize the risk of infection passing from the patient to the CPR giving person which might occur with direct mouth to mouth contact or vice-versa.

DESCRIPTION OF PRIOR ART

A known CPR face mask is described in my U.S. Pat. No. 5,469,842 issued Nov. 28, 1995, and the contents of this patent are hereby incorporated herein by reference. The face mask described in this patent has a flow control valve with an upper inlet into which air can be blown by the CPR giving person to pass downwardly through a first outlet into the patient's mouth, the flow control valve causing air passing upwardly from the patient's mouth into the first outlet to be released to the external atmosphere through a second outlet without passing to the inlet.

In order to further minimize the risk of transmitting infection, it is known to position a suitable filter between the flow control valve and the patient. However, it has been found that with, such an arrangement, the filter causes undesirable resistance to air flow from the patient, especially if the filter has been dampened by condensation from air flow passing to or from the patient.

It is therefore an object of the invention to provide a CPR face mask with an improved filter arrangement.

SUMMARY OF THE INVENTION

According to the invention, the air flow control valve is provided with a suitable filter immediately upstream of a flexible diaphragm which is operable to prevent air flow from the inlet to the second outlet when the CPR giving person is blowing into the inlet and to prevent air flow from the first outlet to the inlet when air passes upwardly from the patient's mouth into the first outlet.

Thus, air passing from the CPR giving person to the patient is filtered, but the air passing from the patient to the external atmosphere is not filtered. The filter positioned in accordance with the invention therefore does not obstruct flow of air from the patient to the external atmosphere and is protected by the diaphragm from condensation from the air exhaled by the patient. An added advantage is that, if the diaphragm becomes faulty and does allow some air to pass from the patient to the CPR giving person, then such air will have to pass through the filter.

Advantageously, the filter is seated in a recess in the medial portion at the junction of an upper tubular portion of the housing providing the inlet and a medial portion of the housing providing a valve chamber which contains the diaphragm.

BRIEF DESCRIPTION OF THE DRAWING

One embodiment of the invention will now be described, by way of example, with reference to the accompanying drawings, of which.

DESCRIPTION OF THE PREFERRED EMBODIMENT

Figure 1:
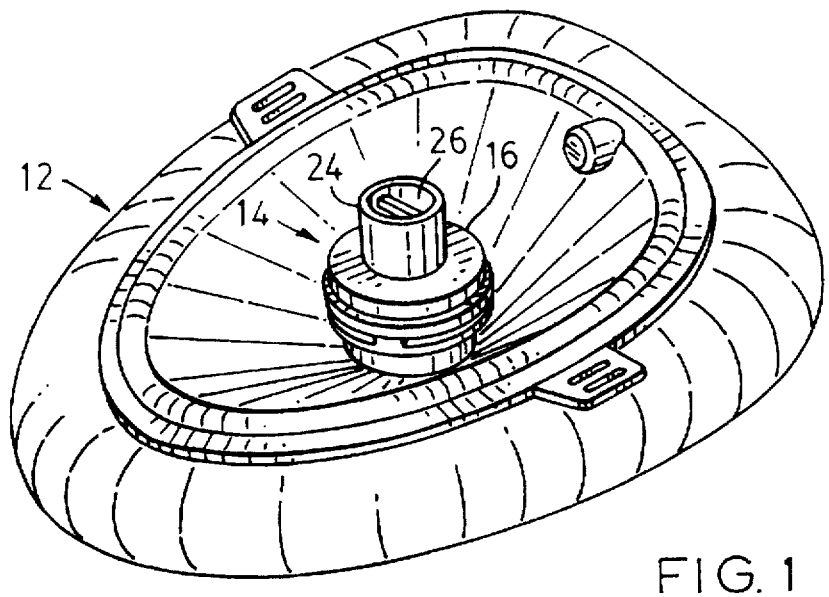
FIG. 1 is a perspective view of a CPR face mask having an air flow control valve in accordance with one embodiment of the invention.

Referring to the drawings, a CPR face mask has a face-engaging part 12 which carries an air flow control valve 14. The flow control valve 14 has a housing 16 formed in three parts of transparent plastic material, namely top part 18, a middle part 20 and a lower part 22.

The top part 18 has an upper tubular portion 24 providing an inlet 26, an annular flange portion 28 surrounding the lower end of the upper tubular portion 24, an annular wall portion 30 extending downwardly from the outer edge of the flange portion 28, and an annular ledge portion 31 surrounding the lower end of the wall portion 30. The lower end of the upper tubular portion 24 and the adjacent part of the annular flange portion 28 have a circular recess 32 in which a circular filter 33 of suitable woven material is seated, the filter 33 being secured in place by a suitable glue.

The middle portion 20 of the housing 16 has an annular disc-like body portion 34 with a central aperture 36 from the edge of which a tubular portion 38 extends downwardly. The body portion 34 also has an aperture 40 of short circumferential extent surrounded by an annular wall 42. The aperture 40 provides a second outlet from the flow control valve 14 (the first outlet will be described later). The body portion 34 has three circumferentially-spaced posts 44, 46, 48 on the opposite side of the aperture 36 to the annular wall 42 for a purpose which will be described later, and also has a short wall 50 extending around the body portion 34 near to but spaced from its periphery (except where interrupted by the wall 42) so as to provide the body portion 34 with a peripheral ledge 52. The top part 18 and the middle part 20 form a valve chamber 54 which contains a flexible diaphragm 56 of rubber-like material.

The lower part 22 of the housing 16 has a disc-like body portion 57 with a central aperture 58 from the edge of which a tubular portion 60 extends downwardly to provide a first outlet 62. The body portion 56 also has three upwardly extending spacers 64 circumferentially spaced around its periphery.

Figure 3:
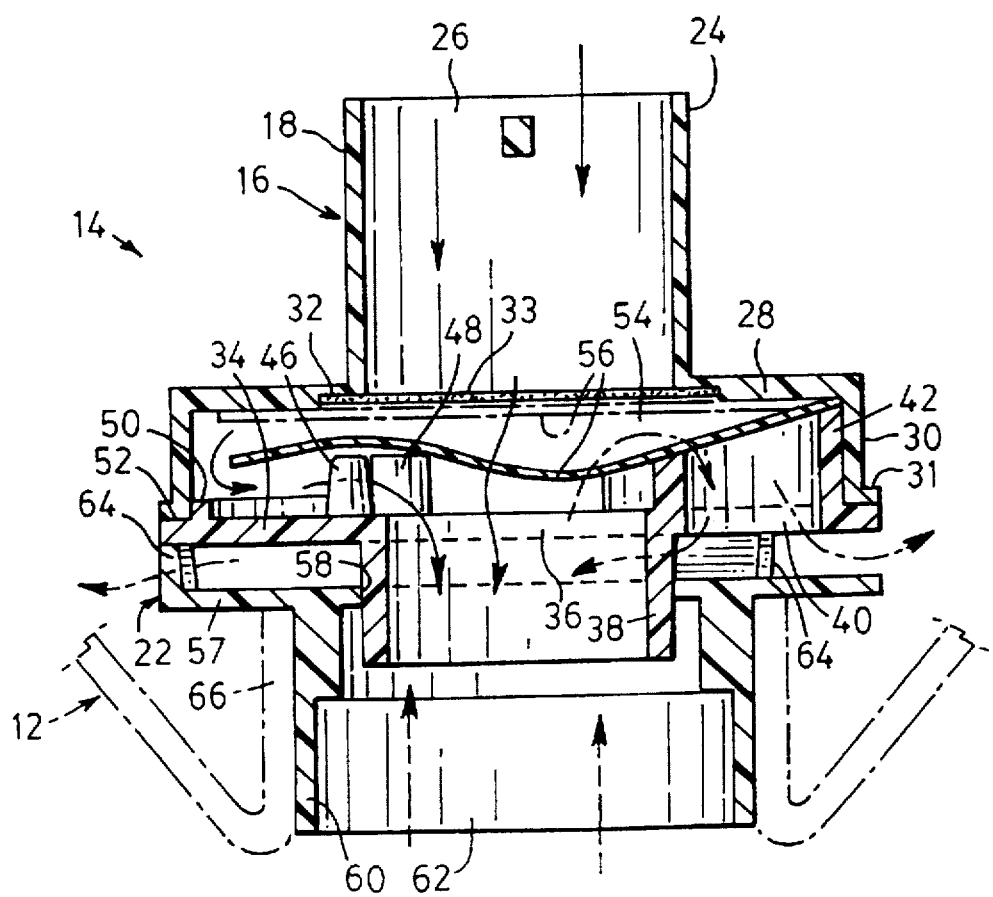
FIG. 3 is an exploded view thereof.
Figure 2:
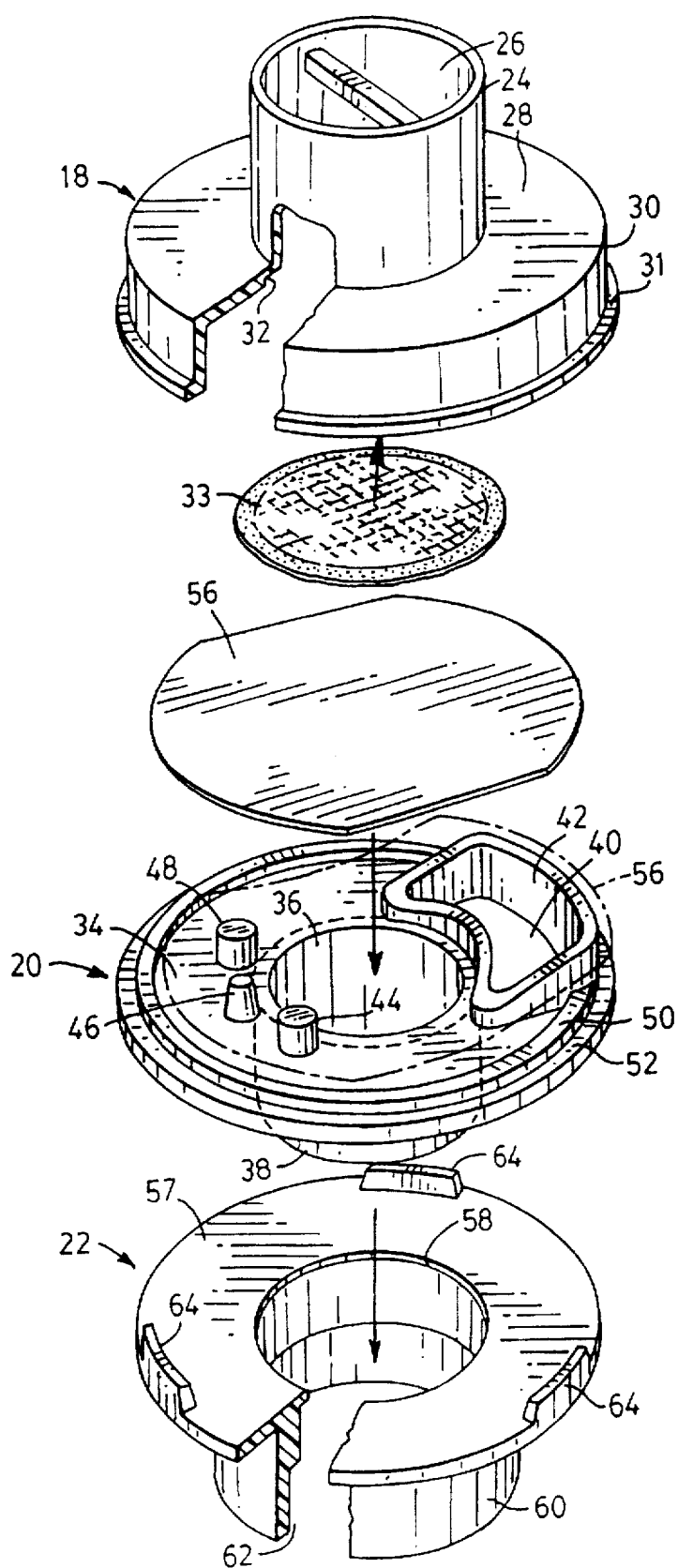
FIG. 2 is a sectional view of the air flow control valve.

The top part 18, the middle part 20 and the lower part 22 of the housing 16 are heat sealed together in the manner show in FIG. 3. The top part 18 fits into the middle part 20 with the annular ledge portion 31 of the top part 18 seating on the peripheral ledge 52 of the middle part 20. The tubular portion 38 of the middle part 20 is a sliding fit in the edge of the aperture 58 of the bottom part 22, with the disc-like body portion 57 of the lower part 22 being spaced from the disc-like body portion 34 of the middle part 20 by the three spacers 64. A side portion of the diaphragm 56 is held between the outer part of the annular wall 42 of the middle part 20 and the flange portion 28 of the top part 18. As also shown in FIG. 3, the tubular portion 60 of the bottom part 20 is a sliding fit in a portion 66 of the face-engaging part 12 of the face mask.

In use, after the face mask 12 has been positioned over the mouth of a patient, the CPR giving person blows into the inlet 26, and the blown air passes through the filter 33 into the valve chamber 54 to cause the diaphragm 56 to engage the top of the annular wall 42 to prevent the blown air from passing to the second outlet 40. The posts 44, 46, 48 hold the diaphragm 56 away from the aperture 36, and hence the blown air passes from the valve chamber 54 downwardly through the aperture 56 and through the first outlet 62 into the patient's mouth. The air flow during this mode of operation is indicated by arrows in full lines and the position of the diaphragm 56 is indicated in full lines in FIG. 3. Thus, air passing from the CPR giving person to the patient is filtered by the filter 33.

When the patient exhales, the exhaled air passes upwardly into the first outlet 62 and into the valve chamber 54 to push the diaphragm 56 upwardly against the filter 33 to prevent exhaled air from passing through the upper inlet 26 into the mouth of the CPR giving person. The upward movement of the diaphragm 56 opens the top of the annular wall 42, and the exhaled air passes from the valve chamber 54 through the second outlet 40 and between the middle part 20 and bottom part 22 (which are spaced by spacers 64) to the external atmosphere. The air flow during this mode of operation is indicated by arrows in dotted lines in FIG. 3, the position of the diaphragm 56 during this mode also being indicated in dotted lines.

Thus, air passing from the CPR giving person to the patient is filtered, but air passing from the patient to the external atmosphere is not filtered. The filter 33 positioned in accordance with the invention therefore does not obstruct flow of air from the patient to the external atmosphere and is protected by the diaphragm 56 from condensation from the air exhaled by the patient. Further, if the diaphragm 56 becomes faulty and does allow some air to pass from the patient to the CPR giving person, then such air will have to pass through the filter 33.

Other embodiments of the invention will be readily apparent to a person skilled in the art, the scope of the invention being defined in the appended claims.

I claim:

1. A CPR face mask having:

a face engaging part positionable on the face of a patient to surround at least the mouth of the patient, an air flow control valve carried by the face engaging part and having an upper inlet into which air can be blown by a CPR giving person and which passes downwardly through a first outlet into a patient's mouth, said flow control valve causing air passing upwardly from the patient's mouth into the first outlet to be released to the external atmosphere through a second outlet without passing to the inlet, said flow control valve having a flexible diaphragm operable to prevent air flow from the inlet to the second outlet when the CPR giving person is blowing into the inlet and to prevent air flow from the first outlet to the inlet when air passes upwardly from the patient's mouth into the first outlet, and a filter immediately upstream of the diaphragm with respect to air flow blown into the first inlet by the CPR giving person, the air flow control valve having a housing with an upwardly extending tubular portion providing said inlet, and means for protecting said filter from patient-expired condensation comprising said diaphragm having a filter-blocking position assumed during patient exhalation and a medial portion providing a valve chamber containing said diaphragm, said diaphragm being moved upwardly by air passing upwardly from the patient during exhalation to prevent air from passing to the inlet and also to engage the filter.

2. A CPR face mask according to claim 1 wherein the medial portion has a recess in which the filter is seated.

3. An air flow control valve for a CPR face mask having:

a housing with an upper tubular portion providing an inlet, and a medial portion below the upper tubular portion providing a valve chamber, a diaphragm in the chamber, the medial portion having a first outlet through which air blown into the inlet passes, with the diaphragm being caused by the flow of air blown into the inlet to close a second outlet from the valve chamber to the external atmosphere and being caused by flow of air blown into the first outlet to close the inlet and permit air blown into the first outlet to pass through the second outlet to the external atmosphere, a filter at the junction of the upper tubular portion and the medial portion so as to be immediately upstream of the diaphragm with respect to flow of air blown into the first inlet and means for protecting said filter from patient-expired condensation comprising said diaphragm having a filter-blocking position assumed during patient exhalation, whereby the diaphragm is moved upwardly by air passing upwardly from the patient during exhalation to prevent air from passing to the inlet and also to engage the filter.

4. An air flow control valve according to claim 4 wherein the medial portion of the housing has a recess in which the filter is seated.

* * * * *